United States Patent [19]

Chauveau et al.

[11] Patent Number: 5,298,491

[45] Date of Patent: Mar. 29, 1994

[54] DERIVATIVES OF ENDOGENOUS MEDIATORS, THEIR SALTS, METHOD OF PREPARATION, APPLICATIONS AND COMPOSITIONS IN WHICH THEY ARE PRESENT

[75] Inventors: Jacques Chauveau; Michel Delaage; Anne Morel; Louis Segu, all of Marseille, France

[73] Assignee: Immunotech, Marseille, France

[21] Appl. No.: 699,027

[22] Filed: May 13, 1991

[30] Foreign Application Priority Data

May 15, 1990 [FR] France ............................. 9006292
Jan. 30, 1991 [FR] France ............................. 9101292

[51] Int. Cl.$^5$ .................. A61K 31/405; C07D 209/16; G01N 21/75
[52] U.S. Cl. .............................. 514/17; 514/18; 514/19; 514/415; 548/504; 252/182.11; 435/7.1; 435/7.9; 436/547; 436/64; 562/451; 530/412
[58] Field of Search ............... 548/504; 252/182.11; 514/17, 18, 19, 415; 435/7.1, 7.9; 436/547, 164; 562/451; 530/412

[56] References Cited

U.S. PATENT DOCUMENTS

| | | |
|---|---|---|
| 2,703,325 | 3/1955 | Speeter et al. ............... 252/182.1 |
| 3,182,071 | 5/1965 | Shavel, Jr. et al. ............... 548/504 |
| 3,801,594 | 4/1974 | Poletto et al. ............... 548/504 |
| 3,878,187 | 4/1975 | Schneider et al. ............... 548/504 |
| 4,040,907 | 8/1977 | Ullman et al. ............... 548/504 |
| 4,046,636 | 9/1977 | Ullmann et al. ............... 548/504 |
| 4,252,803 | 2/1981 | Webb ............... 548/504 |
| 4,331,646 | 5/1982 | Delaage ............... 548/504 |
| 4,426,453 | 1/1984 | Cree et al. ............... 548/504 |
| 4,629,737 | 12/1986 | Cantello ............... 548/504 |
| 4,672,067 | 6/1987 | Coates et al. ............... 548/504 |
| 4,695,580 | 9/1987 | Ohashi et al. ............... 548/504 |
| 4,818,683 | 4/1989 | Morel et al. ............... 548/504 |
| 4,820,860 | 4/1989 | Wissmann et al. ............... 548/504 |
| 4,833,153 | 5/1989 | Dowle et al. ............... 548/504 |
| 4,870,096 | 9/1989 | Oxford et al. ............... 548/504 |
| 4,910,193 | 3/1990 | Buchheit ............... 548/504 |
| 4,933,324 | 6/1990 | Shashoua ............... 548/504 |
| 4,963,546 | 10/1990 | North et al. ............... 548/504 |
| 5,019,586 | 5/1991 | Oxford et al. ............... 548/504 |
| 5,026,696 | 6/1991 | North et al. ............... 548/504 |

FOREIGN PATENT DOCUMENTS

| | | |
|---|---|---|
| 0006792 | 6/1979 | European Pat. Off. ............ 548/504 |
| 0099707 | 7/1983 | European Pat. Off. ............ 548/504 |
| 0161195 | 4/1985 | European Pat. Off. ............ 548/504 |
| 0257572 | 8/1987 | European Pat. Off. ............ 548/504 |
| 0328251 | 1/1989 | European Pat. Off. ............ 548/504 |
| 2737802 | 8/1977 | Fed. Rep. of Germany ...... 548/504 |
| 9006292 | 5/1990 | France ............... 548/504 |
| 9101292 | 1/1991 | France ............... 548/504 |

OTHER PUBLICATIONS

Koehrle, J. et al., "Rat Liver Iodothyronine Monodeiodinase", *Journal of Biological Chemistry* 261:25 (1986).

Boulenguez, P. et al., "A New 5-Hydroxy-Indole Derivative with Preferential Affinity for 5-HT1B Binding Sites", *European Journal of Pharmacology* 194:91–98 (1991).

*Primary Examiner*—Mary C. Lee
*Assistant Examiner*—Joseph K. McKane
*Attorney, Agent, or Firm*—Browdy and Neimark

[57] ABSTRACT

Derivatives of biologically active molecules containing a primary amine group and a hydroxylated nucleus, and their addition salts with mineral or organic acids, having general formula I:

$$R'R''N-A-B-O-CH_2-CO-NH-R \qquad (I)$$

A = linear or branched $C_1$-$C_5$ alkylene;
B = $C_4$-$C_{10}$ aromatic nucleus with optional heteroatom, or = group $-B_1-X-B_2-$, wherein X = O or $C_1$-$C_4$ alkylene;
—NH—R = amine residue or alcohol residue; and
R', R" = $C_1$-$C_5$ alkyl, H or hydrophobic radical, and their addition salts with mineral or organic acids, method of preparation, applications, especially to visualization, purification, the preparation of antibodies and the assay of the total hormone, and as drugs, compositions in which they are present and analytical kits.

18 Claims, 12 Drawing Sheets

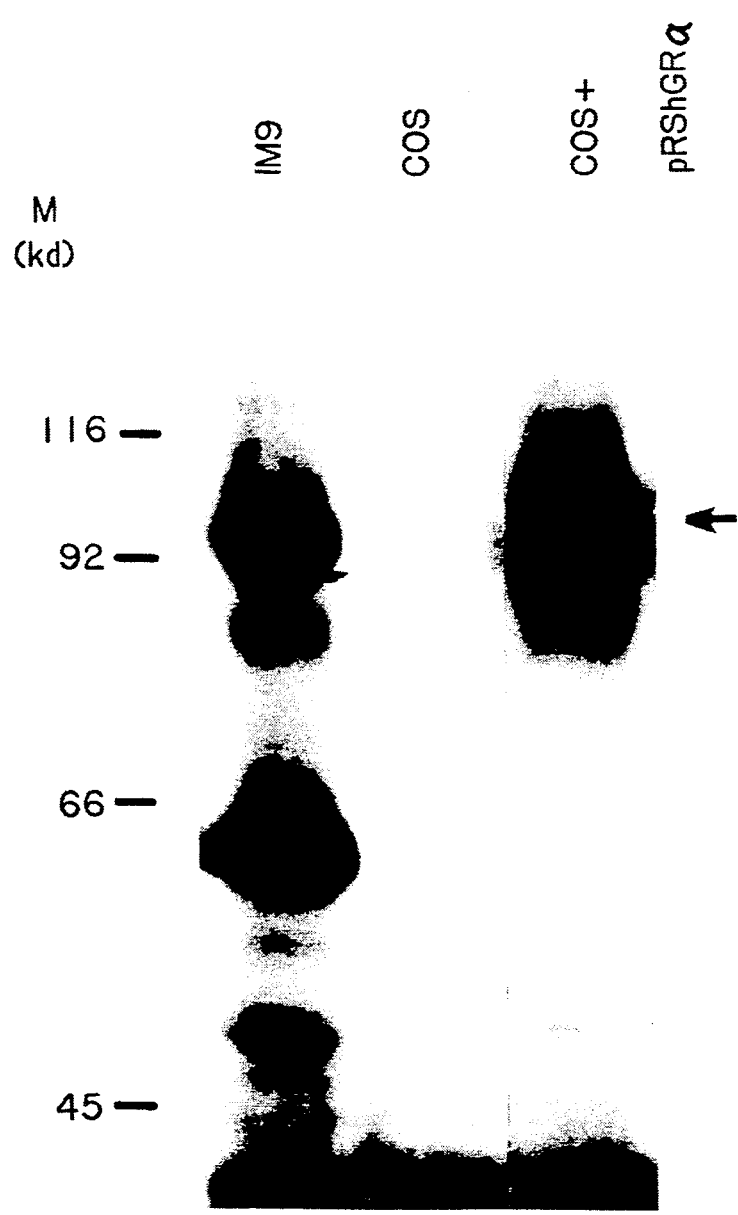

DERIVATIVES OF ENDOGENOUS MEDIATORS, THEIR SALTS, METHOD OF PREPARATION, APPLICATIONS AND COMPOSITIONS IN WHICH THEY ARE PRESENT

The present invention relates to novel derivatives of endogenous mediators, to their salts, to their method of preparation, to their applications, especially to the analysis of endogenous mediators, the analysis or purification of the receptors for said mediators, the visualization of their receptor sites, the preparation of antibodies and the use of said antibodies for the analysis of endogenous mediators, to their application as drugs and to compositions in which they are present.

Messages are transmitted between cells by way of chemical vectors (hormones or neuromediators) whose specificity is assured by the target protein: the receptor. The molecules carrying the information can be peptides or low molecular weight molecules. A number of these simultaneously possess one or more hydroxyl groups and one or more amine groups, for example indolamines, catecholamines (neuromediators) and thyroxine (hormone).

These molecules play a role of prime importance in physiology: indolamines and catecholamines in the transmission and integration of information in the central and peripheral nervous systems, and thyroxine in the regulation of the basal metabolism. It is essential to assay them for the purpose of improving diagnoses or assisting functional researches. In the case of neuromediators, the receptor binding sites assure the specificity of the response of the effector cell: localized chemical modification of the endogenous ligands makes it possible to distinguish between the various types and subtypes of membrane receptor. Thus modified ligands could be drugs acting specifically on the physiological functions controlled by these receptors.

Certain hormones are present in the serum in a form bound to carrier proteins. These proteins ensure that these hormones are transported from the point of synthesis to the target cells. The thyroid hormones are present in an unbound form at levels of less than 1% of the total amount of hormones (free + bound). Localized chemical modification of the thyroid hormones enables their assay to be improved.

The Applicants have discovered that these objectives can be achieved through O-carboxymethylation on the hydroxyphenyl group of endogenous molecules also carrying a primary amine.

Carboxymethylation (Gurd, Methods in Enzymology, vol. XI, 1967, p. 532-541) has often been used to block the amine groups of amino acids. The carboxymethylation of hydroxyphenyl groups is described as a side reaction (Korman and Clarke, J. Biol. Chem., 221, 1956, p. 113-131). The carboxymethylation of hydroxyphenyl groups (Spector, 1982) has been used for coupling morphine (which does not possess an amine group) with a prote-i.n to give an antibody.

It is for this reason that the,present patent applicate-.on relates to novel derivatives of biologically active molecules containing a primary amine group and a hydroxylated nucleus, characterized in that they have the general fornula I:

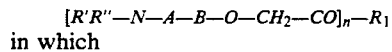
(I)

in which

A is a linear or branched alkylene chain containing from 1 to 5 and preferably 2 carbon atoms, it being possible for the branch to contain a sulphydryl group;

B is an aromatic nucleus containing from 6 to 10 substituted or unsubstituted carbon atoms and, if appropriate, a heteroatom, or a group $-B_1-X-B_2$, in which $B_1$ and $B_2$ are as defined for B above and X is an oxygen atom or an alkylene chain containing from 1 to 4 carbon atoms;

$R_1$ is an amine residue or an alcohol residue; and

R' and R" are an alkyl radical containing from 1 to 5 carbon atoms, a hydrogen atom, an aliphatic acyl radical containing from 2 to 5 carbon atoms, aminoacyl or a hydrophobic radical, as well as their addition salts with mineral or organic acids, it being understood that R' and R" cannot be a radical derived from 2-hydroxy-3-phenoxypropyl or from 2-hydroxy-2-phenylethyl.

The addition salts with mineral or organic acids can be, for example, salts formed with hydrochloric, hydrobromic, nitric, sulphuric, phosphoric, acetic, formic, propionic, benzoic, maleic, fumaric, succinic, tartaric, citric, oxalic, glyoxylic and aspartic acids, alkanesulphonic acids such as methaneor ethane-sulphonic acid, arylsulphonic acids such as benzene- or paratoluene-sulphonic acid, or arylcarboxylic acids. it is preferable to use the salts of chaotropic anions, such as citrate or succinate ions, which are capable of facilitating dissolution in aqueous media.

The alkylene chain represented by A can be a propylene, isopropylene, methylene or, preferably, ethylene chain; it can be substituted by a sulphydryl group.

The aromatic nucleus can contain a single ring, such as a phenyl nucleus, or two rings, such as an indole nucleus for example. One or more of the carbon atoms of B can be substituted by a radical selected from halogen atoms such as chlorine, alkoxy radicals such as ethoxy or, preferably, methoxy, alkyl radicals such as propyl, ethyl or, preferably, methyl, alkylthio radicals such as methylthio, and polyhalogenoalkyl radicals such as trifluoromethyl.

The hydroxyl substituted by the radical $-CH_2-CO-NH-R$ according to the present invention can be located in any position, but is located particularly on a phenyl ring of the nucleus and preferably in the positions which this hydroxyl radical normally occupies in natural mediators.

If R' and R" are an alkyl radical, they are preferably a methyl or ethyl radical. R' and R" are advantageously hydrogen. Aminoacyl radical is understood as meaning amino acid residues, peptides or proteins. Hydrophobic radical is understood as meaning that said radical possesses saturated chains and does not contain groups such as free amino or hydroxyl groups.

R' and R" are advantageously a hydrogen atom or a methyl or ethyl radical, it being possible for the radical NR'R" to be quaternized, if appropriate, and examples which may be mentioned are trimethylammonium or diethylmethylammonium radicals.

R' and R" are also especially a tyrosyl or lysyl radical.

In the group $-B_1-X-B_2$, $B_1$ and $B_2$ are preferably a phenyl nucleus which is unsubstituted or substituted by one or more radicals such as halogen atoms, especially iodine atoms, or the other radicals described above for the nucleus B.

If X is an alkylene chain, it preferably comprises two or, preferably, only one carbon atom.

In the case where $R_\cdot$ is an amine residue, symbolized by $-NH-R$, the residue R, which is therefore attached to the carboxyl by an amide bond, can be of any type but is preferably a residue suitable for labelling, for example with one or more radioactive atoms such as $^{125}I$.

The chemical type of this residue R will preferably include an amino acid, which will be used for bonding with the rest of the molecule of formula (I). This amine residue will be for example a protein or a polypeptide containing from 2 to 10 amino acids and preferably 2 or 3 amino acids, or else a monoamino such as tyrosine, or a diargino acid.

Said amino acids will preferably be natural amino acids or their amide derivatives; thus, for example, if the radical $R_1$ is a dipeptide consisting of a glycyl residue and a tyrosyl residue, it may be possible, for example, to replace the tyrosyl residue with a tyrosinamide residue.

The diamine may be used for the coupling of fluorophores or for the synthesis of dimers of formula (I'):

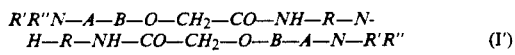

$$R'R''N-A-B-O-CH_2-CO-NH-R-N-H-R-NH-CO-CH_2-O-B-A-N-R'R'' \quad (I')$$

in which R, R', R", A and B are as already defined.

Among the amine residues, there may be mentioned especially amino, hydrazino and nitrilo ($-N_3$) residues and the following peptides or peptide derivatives: tyrosyl-cysteine, tyrosyl-cysteinamide, tyrosylglycine or tyrosyl-glycinamide.

There may also be mentioned protein derivatives joined to the carboxyl directly or via a peptide or an amino acid and via a heterobifunctional agent capable of reacting with a sulphydryl group and an amino group, such as SMCC, and the following residues may be mentioned as examples: tyrosyl-cysteinyl-protein, tyrosyl-cysteinyl-heterobifunctional agent such as (SMCC)-protein, glycyl-tyrosine or glycyl-butane-1,4-diamine.

In the case where $R_1$ is an alcohol, (II):

$$R'R''N-A-B-OH \quad (II)$$

in which R', R", A and B are as already defined, is reacted with a derivative containing a protecting group for the amine groups in the case where R'=R"=H, to give a derivative of formula (III):

$$Y-HN-A-B-OH \quad (III)$$

in which A and B are as already defined and Y is a readily cleavable protecting group for the amine groups, which is reacted with a halogenoacetic acid to give a derivative of formula (IV):

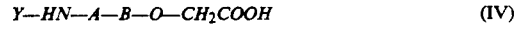

$$Y-HN-A-B-O-CH_2COOH \quad (IV)$$

in which A, B and Y are as already defined, which is reacted with an amine derivative or an alcohol to give either the Cierivative of formula (I) as defined above, a dimer of formula (I'):

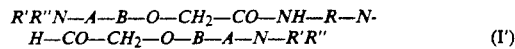

$$R'R''N-A-B-O-CH_2-CO-NH-R-N-H-CO-CH_2-O-B-A-N-R'R'' \quad (I')$$

in the case of a diamine, or a polymer in the case of a polyamine, which is isolated and, if desired, converted to a salt.

The derivatives of general formula I have a basic character. Salts of the derivatives of general formula I can advantageously be prepared, if appropriate, by reacting a mineral or organic acid with said derivative of general formula I in approximately stoichiometric proportions. If appropriate, the salts can be prepared without isolation of the corresponding bases.

The derivative capable of grafting a protecting group for the amine groups on to the derivative of formula (II) can be, for example, an acid chloride [9fluorophenylmethyloxycarbonyl chloride (FmocCl) or benzyloxycarbonyl chloride (BzCl)] or, preferably, an anhydride [di-t-butyl dicarbonate, $(BOC)_2O$, or citraconic anhydride]. there are derivatives of phenols which are unsubstituted or substituted on the phenyl, such as 2- or 4-nitrophenol, those derived from phenylmethanol which are unsubstituted or substituted on the phenyl by an alkyl radical, those derived from hydroxyalkyltrimethylsilyl, especially hydroxyethyltrimethylsilyl, and those derived from $C_1-C_{16}$ aliphatic alcohols.

Preferred derivatives according to the invention are derivatives of formula (I) as defined above which are characterized in that B is a phenyl nucleus, a p-phenoxyphenyl group which is unsubstituted or substituted by one or more halogen atoms, especially a 4-(3,5-diiodophenoxy)-3,5-diiodophenyl group, or an indole nucleus, and their addition salts with mineral or organic acids. The nuclei can be substituted by a halogen atom, preferably chlorine, bromine or iodine, especially the indole nucleus, in which case substitution is preferably in the 2-position.

Among these derivatives in which B is an indole nucleus, it is particularly preferred to ube those which are characterized in that $R_1$ is a diamine, a protein, an amino acid or a polypeptide consisting of at most 5 amino acids, or derivatives of said amino acids or polypeptides, and especially tryptamine-5-O-carboxymethylglycyltyrosinamide [S-CM-GTNH$_2$], as well as the derivatives mentioned in the Examples, and their addition salts with mineral or organic acids.

Among these derivatives, it is also preferred to use those which are characterized in that A is a radical $-(CH_2)_2-$ and R' and R" are a linear or branched alkyl radical containing from 1 to 5 carbon atoms.

The present patent application further relates to a method of preparing the derivatives described above, characterized in that a derivative of formula The derivative of formula (IV) is preferably prepared at alkaline pH in the presence of a metal oxide, such as magnesium oxide, and a halogenoacetic acid, it being possible f or the latter to be a chloride, although it is preferably a bromide.

The reaction of the derivative of formula (IV) with the amine derivative ($R_1$) is preferably carried out after activation of the carboxyl group in the form of a mixed anhydride by means of an alkyl chlorocarboxylate such as ethyl chlorof ormate. It is also possible to use acid chlorides and carbodiimides as activators or to form a hydrolyzable N-hydroxysuccinimide ester beforehand. If necessary, the protecting group for the amine is cleaved by acid hydrolysis, especially with an acid such as trifluoroacetic acid, or by alkaline hydrolysis, especially with piperidine.

The mediators of formula (II) and their synthetic analogues are well known from various publications and patents.

The derivative of formula (I), or one of its salts" can be coupled with a marker through the presence of a free carboxyl group in the residue $R_1$ in formula I, as described for the bonding of the amine residue to the rest of the molecule of formula I.

If the marker is iodine, the residue $R_1$ will contain a tyrosine (or a tyrosinamide) or a histamine.

If the marker is an enzyme, the residue $R_1$ will contain carboxyl or sulphydryl groups.

If the marker is a fluorescent element, the gresidue $R_1$ will contain a diamine.

Of the derivatives of formula I described above, we emphasize those which contain a protein grafted on to the O-carboxymethyl unit in accordance with the above methods.

The derivatives forming the subject of the present invention possess very valuable pharmacological properties. In particular, indole derivatives possess a remarkable affinity for serotonin receptors, especially the 5HT1D'S.

These properties are illustrated below in the experimental section. They justify the use of the mediator derivatives described above, and their addi tion salts with pharmaceutically acceptable acids, as drugs.

The drugs according to the present invention are employed for example in both the curative and preventive treatment of diseases associated with a dysfunction of the 5-HT receptors (particularly 5HT1D'S), their deregulation or modifications of the endogenous ligand (generally serotonin). They are employed in particular in the treatment of migraine.

The customary dose, which varies according to the subject treated and the complaint in question, can be for example from 0.1 to 10 mg per day, administered orally to man, of the derivative of Example 1.

The invention further relates to the pharmaceutical compositions which contain at least one of the aforementioned derivatives, or one of its addition salts with pharmaceutically acceptable acids, as the active principle.

As drugs, the derivatives of general formula I and their addition salts with pharmaceutically acceptable acids can be incorporated into pharmaceutical compositions intended for the digestive tract or for parenteral administration.

These pharmaceutical compositions can be solid or liquid, for example, and can be presented in the pharmaceutical forms commonly used in human medicine, such as, for example, simple or coated tablets, gelatin capsules, granules, sx,1/27eets suppositories, preparations for nasal instillation and injectable preparations; they are prepared in accordance with the customary methods. In said compositions, the active principle or principles can be incorporated into excipients normally employed in pharmaceutical compositions, such as talc, gum arabic, lactose, starch, magnesium stearate, cocoa butter, aqueous or non-aqueous vehicles, fats of animal or vegetable origin, paraffinic derivatives, glycols, various wetting agents, dispersants or emulsifiers, and preservatives.

As has been seen, the derivatives of formula (I) possess a substantial affinity for the receptors or else the carrier protein for the corresponding endogenous molecule.

The derivatives, forming the subject of the present patent application, which may or may not be labelled, for example with a radioactive element, especially $^{125}I$, or a fluorescent element or with an enzyme, are particularly useful for the visualization, both in vitro and in some cases in vivo, of endogenous mediator binding sites. These are illustrated below in the experimental section. A protein carrying a colloidal gold or a contrast medium can also be used as a marker.

The prasent patent application therefore further relates to the derivatives described above which are characterized in that they are in a labelled form.

The present patent application further relates to the use of the derivatives described above in the purification of endogenous mediator receptors.

The O-carboxymethylation of thyroid hormones modulates the interaction of these hormones with their carrier proteins. This property can be utilized to eliminate the binding of these native thyroid hormones to these carrier proteins. In the context of an immunoanalytical activity, the creation of analogues not recognized by the antibody, which inhibit binding to the carrier proteins, makes it possible to assay the total hormone.

The present patent application further relates to the application of the derivatives described above, and in particular the 0-carboxymethylated derivatives of thyroxine, to the inhibition of binding to carrier proteins, for the purpose of assaying the total hormone.

The derivatives of the present patent application in which $R_1$ is a protein make it possible to prepare antibodies directed against the mediator corresponding to the rest of the molecule of formula (I).

The present patent application further relates to the application of the derivatives described above to the visualization of endogenous mediator binding sites.

The present patent application further relates to the application of the derivatives of formula (I) to the preparation of antibodies directed against endogenous mediators.

The endogenous mediators [of formula (II), R'R''—N—A—B—OH] or their derivatives may be assayed by means of these antibodies, using the derivatives of formula (I) as a tracer.

The present patent application finally relates to analytical kits, characterized in that they contain at least one of the derivatives of formula (I) described above.

The Examples which follow illustrate the present invention without however implying a limitation.

EXPERIMENTAL SECTION

Example 1. Synthesis of Thyroxine Derivatives

Series of examples of general formula I:

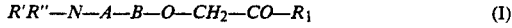

$$R'R''—N—A—B—O—CH_2—CO—R_1 \qquad (I)$$

in which $R'=R''=H$, $A=$ —CH(COOH)—CH$_2$— and B is of the type —$B_1$—X—$B_2$—, where X=oxygen; if $B_1=B_2=C_6H_2I_2$: derivatives of 3,3',5,5'-tetraiodo-L-thyronine or L-thyroxine (T$_4$); if $B_1=C_6H_2I_2$ and $B_2$ $C_6H_3I$: derivatives of 3,3',5-triiodo-L-thyronine (T$_3$).

Stage A

1. Synthesis of N-tert-butylcarbamate-O-carboxymethyl—T$_4$ (BOC—T$_4$—O—CH$_2$—COOH) or —T$_3$ (BOC—T$_3$—O—CH$_2$COOH)

1.1. Protection of the amine group

For the syntheses of Example 1, T$_4$ or T$_3$ is used in the form of the free acid or the acid modified for example by amidation.

The amine group of T$_4$ and T$_3$ is protected with di-t-butyl dicarbonate [(BOC)$_2$O] (Tarbell et al., Proc. Nat. Acad. Sci. U.S.A., 69, 1972, 730-732). 30 μl of triethylamine (TEA, 7.2N) and 240 μl of 50 mM (BOC)$_2$O in dimethyl sulphoxide (DMSO) are added to 10 μmol of T4 or T3.

1.2. Carboxymethylation of the hydroxyphenyl group

The solution obtained above is mixed in equal volumes with a 500 mM aqueous solution of bromoacetic acid, with the pH adjusted to 12, in the presence of magnesium oxide and nitrogen gas. The mixture is stirred for 24 h in the dark. The medium is centrifuged for 10 minutes at 10,000 rpm.

1.3. Purification of the products by high performance liquid chromatography (HPLC)

The supernatant is diluted in 5 volumes of 0.05% trifluoracetic acid (TFA). One ml of this mixture is injected into a column of μ Bondapack C18 grafted silica (10 μm, diameter 3.9 mm, length 30 cm). The derivatives of T3 are eluted isocratically for 30 min with a mixture of 50 vol. of 0.05% TFA and 50 vol. of methanol, and then with a gradient reaching 100% of methanol in 60 minutes. For the derivatives of T4, the initial mixture for isocratic elution is composed of 40 vol. of 0.05% TFA and 60 vol. of methanol. The flow rate is 1 ml/min.

The starting materials (T3, T4) are collected during the isocratic period. The substituted derivatives are collected in the gradient:
BOC—T3: 75% of methanol
BOC—T3—O—CH2—COOH: 78% of methanol
BOC—T4: 80% of methanol
BOC—T4—O—CH2—COOH: 82% of methanol
(FIG. 1)

The fractions collected are analyzed by two spectrophotometry. The absorption spectra in basic and acidic media are compared in order to determine whether substitution has indeed taken place on the hydroxyl group (Korman Clarke, Op. cit.). The O-carboxymethylated derivatives do not show any spectral shift in basic media (FIG. 1). The fractions containing the derivatives BOC—T3—O—CH2—COOH and BOC—T4—O—CH2—COOH are evaporated and lyophilized.

2. Conjugation of the O-carboxymethylated derivatives with the radical R—NH2

2.1. Extension of the newly created side-chain

An amide bond can be created between the carboxymethyl group and an amino acid, a peptide chain or a native or modified protein.

The carboxyl group of BOC—T3—O—CH2—COOH or BOC—T4—O—CH2—COOH is activated by ethyl chloroformate (ECF, 7 μl, to which are added 7 μl of TEA in 5 ml of dimethylformamide). This solution is poured on to the lyophilizate in a volume such that the ECF is equimolar with the product to be activated. After activation for 5 min at 4° C., an equal volume of an aqueous solution of NH2—R, at a concentration 50 times greater than that of the carboxymethylated derivative, is added. NH2—R can be histamine, Gly-Tyr, Tyr-Gly, Cys or Gly-Cys, in the form of the free acid or the amide.

The products are separated by HPLC on a column of μ Bondapack C18 in a 0.05% TFA/methanol gradient.

2.2. Preparation of macromolecular derivatives 2.2.1. Grafting of the derivatives BOC—T3—O—CH2—CO—NH—R on to proteins The derivatives as obtained in 1.3. or 2.1. above, or in the form of the free acid, are activated by ethyl chloroformate (see 2.1.) and grafted on to a native protein (BSA, bovine serum albumin) or modified protein (Gly-BSA).

The derivatives BOC—T3—O—CH2—CO—NHR are separated by dialysis from the derivatives coupled with BSA, of the type BOC—T3—O—CH2—CO—NH—R—BSA, where
R=His, Gly-Tyr, Tyr-Gly, Cys, Gly-Cys.

The amine group of these derivatives can be deprotected in accordance with 3.

2.2.2. Grafting of the derivatives T3—O—CH2—CONH-Cys or T3—O—CH2—CONH-Gly-Cys on to proteins Proteins are modified by the addition of a heterobifunctional crosslinking agent of the N-hydroxysuccinimide type, for example succinimidyl-4-(N-maleimidomethyl)cyclohexane-1-carboxylate (SMCC). The reaction "Ishikawa et al., 1983, J. Immunoassay, 4, 209-327) takes place at pH 7.3 in phosphate buffer. The protein whose NH2 residues are activated in this way is separated out by dialysis.

The derivatives T3—O—CH2—CONH—Cys or T3—O—CH2— CONH-Gly-Cys (amidated) are conjugated via the sulphydryl group to the modified proteins at pH 6.5.

The products are separated by dialysis to give derivatives of the general formula T3—O—CH2—CO—NH—Cys—S—SMCC—BSA.

3. Preparation of O-carboxymethylthyroxine (T4—O—CH2—COOH)

The amine group is deprotected by the addition of 200 μl of TFA (200 mg) to the derivative BOC—T3—O—CH2—COOH or BOC—T4—O—CH2—COOH, which has been lyophilized and cooled to −20° C. After a reaction time of one minute, the TFA is evaporated off under nitrogen gas.

Stage B

4. Iodination of the Derivatives 1 mCi of [125I]Na (2000 Ci/mmol, NEN) and 10 μl of chloramine T (CT, 1 mg/ml) are added to 1 nmol of T3, BOC—T3 or BOC—T3—O—CH2—COOH. After 90 sec, the reaction is stopped by 50 μl of sodium metabisulphite (SMB) over a period of 2 min. After the addition of 20 μl of methanol and stirring, the mixture is diluted in 1.5 ml of TFA (0.05%).

The reaction products are separated in accordance with the protocol described in A.1. for the derivatives of Example 1. The products are excluded in the methanol gradient at the following respective concentrations: [125I]T4, 62%; BOC[125I]T4, 80%; BOC[125I]T4—OCH2COOH, 82%.

The radiolabelled derivatives are diluted in methanol. The BOC[125I]T4—O—CH2—COOH is deprotected as indicated in 3.

Example 2. Synthesis of Serotonin Derivatives

Series of examples of general formula I:

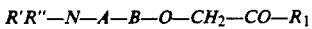

in which R'=R"=H, A=—CH2—CH2— and B= indole nucleus (OH in 5-position, aminoethyl in 3-position).

1. Synthesis of N-tert-butylcarbamate-5-O-carboxymethyltryptamine [BOC-S-CM]

Derivative of standard formula (IV): Y—HN—A—B—O—CH2—COOH.

Stage A

1.1. Protection of the Amine Group

The amine group of 5-HT is protected with di-t-butyl dicarbonate [(BOC)$_2$O] (Tarbell et al., 1972). Equal volumes of 50 mM serotonin oxalate and 50 mM (BOC)$_2$O in dimethyl sulphoxide (DMSO) are mixed in the presence of triethylamine (TEA). The reaction leading to BOC—S is instantaneous at room temparature.

1.2. Carboxymethylation of the hydroxyphenyl group

Protection with BOC is not necessary for certain serotonin derivatives which, like bufotenine, possess a tertiary amine, the residues R' and R" in the general formula being methyl groups. As the rest of the molecule (residues A and B) is identical to serotonin, the O-carboxymethylation of bufotenine can be carried out directly under the same conditions as those described below for BOC—S.

The solution obtained in 1.1. above (Example 2) is mixed in equal volumes with a 500 mM aqueous solution of bromoacetic acid, with the pH adjusted to 12, in the presence of magnesium oxide and nitrogen gas. The pH and the absence of oxygen and light are kept constant for 24 hours. The medium is centrifuged for 5 min at 10,000 rpm.

1.3. Purification by high performance liquid chromatography (HPLC)

The derivative carboxymethyl-O-5-tryptamine—BOC (BOC-S-CM) is separated from the serotonin—BOC (BOC—S) and the oxidation products by HPLC.

The supernatant is diluted in two volumes of a 1% aqueous solution of trifluoroacetic acid. 1.8 ml of this mixture are injected in HPLC on to a column of Ultrasphere ODS C$_{18}$ grafted silica (5 μm, diameter 4.6 mm, length 15 cm) with isocratic elution (55 vol. of H$_2$/0.05% TFA, 45 vol. of methanol). Elution is followed by spectrophotometry.

The carboxymethylation products of bufotenine are separated on a column of μ Bondapack C$_{18}$, isocratic elution being carried out with 93 vol. of 0.05% TFA and 7 vol. of acetonitrile.

The fractions collected are analyzed by spectrophotometry. The absorption spectra in basic and acidic media are compared in order to determine whether substitution has indeed taken place on the hydroxyl group (Korman Clarke, op. cit.).

The fractions containing the derivative BOC-S-CM are evaporated and lyophilized.

2. Conjugation of O-carboxymethylated derivatives with the radical R—NH$_2$

2.1. Extension of the newly created side-chain

An amide bond can be created with a peptide chain after activation of the acid group of BOC-S-CM by ethyl chloroformate (ECF).

The activating solution is composed of 5 ml of dimethylformamide (DMF), 7 μl of TEA and 7 μl of ECF. This solution is poured on to the lyophilized derivative BOC-S-CM in a volume such that the ECF is equimolar with the BOC-S-CM.

After activation for 5 minutes at 4° C., an equal volume of an aqueous solution of glycyl-tyrosinamide (or histamine, Tyr-Gly, Gly-Tyr, Gly-Gly or Gly-Cys, in the form of free or amidated acids), at a concentration 50 times greater than that of BOC-S-CM, is added.

The reaction products are separated by HPLC on a column of Ultrasphere ODS C$_{18}$ by isocratic elution (60 vol. of H$_2$O pH 6, 40 vol. of methanol).

The fractions containing the derivative serotonin-peptide (BOC—S-CM-GTNH$_2$)are evaporated and lyophilized.

2.2. Preparation of macromolecular derivatives

2.2.1. Grafting of derivatives BOC—S-CM-R on to protein

The derivatives as obtained in 1.3. or 2.1. above, or in the form of the free acid, are activated by ethyl chloroformate (see 2.1.) and grafted on to a native protein (BSA) or modified protein (Gly-BSA).

The derivatives BOC—S-CM-R are separated by dialysis from the derivatives coupled with BSA, of the type BOC—S-CM-R—BSA.

The amine group of these derivatives can be deprotected in accordance with 3. above.

2.2.2. Grafting of derivatives S-CM-Gly-Cys on to proteins

Proteins are modified by the addition of heterobifunctional agents (see 2.2.2. of Example 1).

The derivative S-CM-Gly-Cys is grafted on to the above proteins via the sulphydryl group.

The products are separated by dialysis to give derivatives of the type S-CM-Gly-Cys—S—SMCC-BSA.

3. Deprotection of the amine group

200 μl of TFA (200 mg) are poured on to the derivative of the type BOC—S—CO—NHR (where R=H, Gly-TyrNH$_2$, His, Gly-TyroH, Tyr-GlyNH$_2$, Gly-GlyOH, GlyCys), which has been lyophilized and cooled to −20° C. After a reaction time of one minute, the TFA is evaporated off under nitrogen gas.

The reaction products are separated by HPLC on a column of Ultrasphere ODS C$_{18}$ by isocratic elution (65 vol. of 0.05% TFA in water, 35 vol. of methanol).

The fractions containing the derivative possessing the free amine group (S-CM-GTNH$_2$) are evaporated and lyophilized.

Stage B

4. Iodination of the derivatives S-CM-R

If the radical R contains a histamine or a tyrosine, it is possible to carry out iodination with chloramine T.

1 mCi of $^{125}$INa (2000 Ci/mmol, NEN) and 20 μl of CT (1 mg/ml) are added to 10 μl of S-CM-R (1 nmol in PBS medium). After 90 seconds, the reaction is stopped by 50 μl of 50 mM SMB. The mixture is diluted in 1.6 ml of 1% TFA.

The reaction products are separated by HPLC on a column of μ Bondapack C$_{18}$ by isocratic elution (72 vol. of 0.05% TFA in water, 28 vol. of methanol).

The fractions obtained are counted by gamma spectrometry and diluted in a Krebs solution.

I Characteristics of the Binding of Thyroxine derivatives to thyroxine binding proteins The derivatives of stage B of Example 1 (0.1 μl) are added to normal human serum (100 μl). Precipitation is induced by 500 μl of dextran charcoal for 5 min at 4° C. After centrifugation for 10 min at 1000 rpm, the activity of the PELLET is counted.

The binding which persists relative to the initial binding is 99.9% for [$^{125}$I]T$_4$, 80% for BOC[$^{123}$I]-T$_4$—O—CH$_2$—COOH and 75% for [$^{125}$I]T$_4$—O—CH$_2$—COOH.

II Study of the Binding of Serotonin Derivatives to Central Receptors

The test was performed with the product of Example 2, stage B.

The distribution of the receptor binding sites with a high affinity for serotonin (5-HT$_1$) is heterogeneous in the central nervous system of the rat (Pazos and Palacios, Brain Research, 346, 1985, p. 205–230; Ségu et al., Brain Research, 384, 1986, p. 205–217). Furthermore, the content of subtypes of 5-HT$_1$ sites varies according to the anatomical structure in question.

The protocol for preparing the brain sections is common to all the studies which follow. The animals are decapitated after anaesthesia with chloral hydrate (400 mg/kg of gross weight). The brains are quickly removed from the skull and frozen by immersion in isopentane cooled by liquid nitrogen. 20 μm sections, prepared in a cryostat at −20° C., are mounted on gelatin-coated slides and stored at −20° C.

The sections are preincubated for 1 hour at 4° C. in a Krebs solution (NaCl 118 mM; KCl 4.8 mm; CaCl$_2$ 1.2 mM; MgCl$_2$ 1.2 mM; Tris-HCl 15 mM, pH 7.4) in order to remove the endogenous ligands.

1. Displacement, by the derivatives S-CM-R, of the high affinity binding of serotonin in rat brain sections 1.1. Protocol for incubation of the sections The incubations take place for 60 minutes at 20° C. in a Krebs solution containing 10 μM pargyline, 5.7.10$^{-4}$M ascorbic acid, 2 nM [$^3$H]5-HT (NEN, As=30 Ci/mmol) and increasing concentrations of derivatives S-CM-R. The non-specific binding is determined on homothetic sections under the same conditions, but in the presence of 10$^{-5}$M 5-HT.

After incubation, the sections are rinsed three times for 20 seconds in distilled water and dried by a stream of hot air. The sections are affixed to a film (Amersham) for 6 weeks in the presence of a standard ([$^3$H] microscale, Amersham). The films are developed for 6 minutes with Kodak D19, rinsed and fixed with AL4 (Kodak). Quantitative analysis of the autoradiographs is performed with an image analysis system (Ségu et al., J. Neurosci. Methods, 31, 1990, p. 197–208).

1.2. Results

The specific binding of [3H]5-HT is displaced in a one-phase process by 5-HT with an IC$_{50}$ of 2 nM. S—O—CH$_2$—COOH (S—CM) displaces it with an IC$_{50}$ of 1000 nM and S-CM-Gly-TyrNH$_2$ and S-CM-Tyr-GlyNH$_2$ displace the binding in a two-phase process with IC$_{50}$ values of 20 nM for the first site and 400 nM for the second.

2. Analysis of the binding sites for iodinated derivatives on rat central receptors 2.1. Protocol for incubation of the sections The incubations take place for 60 minutes at 20° C. in a Krebs solution containing 10 μM pargyline, 5.7.10$^{-4}$M ascorbic acid, 10 g/l of bovine serum albumin (fraction V, Sigma) and 0.03 nmol/l of the derivative S—CM-[$^{125}$I]—R. The non-specific binding is determined on homothetic sections under the same conditions, but in the presence of 10$^{-5}$M 5-HT.

After incubation, the sections are rinsed twice for 1 min in distilled water and dried by a stream of hot air. The sections are affixed to a kilm (Amersham) for one week in the presence of standards ([$^{125}$I] microscale, Amersham). The films are developed for 6 min with Kodak D19, rinsed and fixed with AL4 (Kodak). Quantitative analysis of the autoradiographs is performed with an image analysis system (Ségu et al., op. cit.).

2.2. Distribution of the labelling with S—CM[$^{125}$I]R fractions 2.2.1. Labelling with S—CM[$^{125}$I]His The fractions of the preparation of the derivative S—CM[$^{125}$I]His (A.4.) do not label rat brain sections.

2.2.2. Labelling with S—CM-G[$^{125}$I]TNH$_2$

Of the fractions collected during the preparation of the iodinated derivative of S-CM-GTNH$_2$ (A.4.), only the last fraction is retained specifically on rat brain sections. This fraction corresponds to S-CM-G]$^{125}$I]TNH$_2$.

Observation of the autoradiographs shows, in the mesencephalic region, intense labelling of the substantia nigra (SN) and the dorsal subiculum (SD) and no labelling of the hippocampus (H). This last structure is known for containing almost exclusively binding sites of the 5-HT$_{1A}$ type, whereas the others contain sites of the 5-HT$_{1B}$ type (Hoyer et al., Eur. J. Pharmacol., 118, 1985, P. 1–12). In the anterior region, the striatum (ST) is labelled: it contains especially 5-HT$_{1B}$ sites; the choroid plexus (Px), which contains 5-HT$_{1c}$ sites, is not labelled.

The conclusion which can be drawn is that S—CM-G[$^{125}$I]TNH$_2$ is a specific marker for binding sites with a high affinity for serotonin of the 1B type.

3. Analysis of binding sites for S—CM-G[$^{125}$I]TNH$_2$ in the guinea-pig

In the central nervous system of the guinea-pig, the anatomical structures containing sites of the 5-HT$_{1A}$ type and the pharmacology of these sites are the same as in the rat. By contrast, the pharmacology of the sites contained in the substantia nigra of the guinea-pig is different from that of the sites of the same structure in the rat (Heuring and Peroutka, J. Neurosci., 7, 1987, p. 894–903). These sites are therefore denotedas 5-HT$_{1D}$.

With the same method of treating the sections as that used in 2. for the rat, it was demonstrated that in the guinea-pig (FIG. 6), S—CM-G[$^{125}$I]TNH$_2$ labels the substantia nigra (FIG. 6C) and not the hippocampus (FIG. 6B).

S—CM-G[$^{125}$I]TNH$_2$ is a marker for sites with a high affinity for serotonin of the 1D type.

This 5-HT derivative has a preferential affinity for the 5-HT$_{1B}$ and 5-HT$_{1D}$ sites compared with the 5-HT$_{1A}$ and 5-HT$_{1C}$ sites, making this ligand an important tool for analyzing receptors with a high affinity for 5-HT.

It is currently the only ligand to exhibit such a high selectivity without binding to other receptors which are not of the 5-HT type (such as β-adrenergic receptors). Furthermore, it is the only ligand to label the 5-HT$_{1D}$ sites. It can therefore be used to study receptors of this type in man and their variation in neurodegenerative diseases (Huntington's chores).

4. Analysis of binding sites in the monkey

The test was performed with the derivative of Example 2, stage A.

A. Biological Preparation

A male monkey (Macacca mulatta n.) weighing 8 kg was sacrificed by means of an overdose of barbiturates and exsanguination. Once the animal's death has been established, the skull is removed and the brain is revealed. The right hemisphere is cut out and frozen by isopentane cooled in liquid nitrogen. The block is stored at −20° C. 10 μm thick sections are prepared in a cryostat at −20° C. and placed on gelatin-coated slides (Ségu et al., 1990, J. Neurosci. Meth., 31, 197). They are stored at −20° C. until required.

Incubation with the Radioactive Probe

The sections are preincubated for 1 h at 4° C. in a Krebs solution (mM: NaCl, 118; KCl, 4.5; CaCl$_2$, 1.2; MgCl$_2$, 11.2; Tris, 15; pH 7.4) in order to remove the endogenous ligands. They are then incubated at 20° C. for 60 minutes in a solution containing $10^{-5}$M pargyline, 57 mM ascorbic acid, 10 g/l of bovine serum albumin and 0.02 nM S—CM-G[$^{125}$I]TNH$_2$, alone or in the presence of increasing concentrations of serotonin. Some of the sections are incubated under identical conditions except that the radioactive probe is replaced either with 2 nM [$^3$H]5-HT, or with 2 nM [$^3$H]5-HT in the presence of 100 nM 8-hydroxy-2-[di-N-propylamino]tetralin (8-OH-DPAT) and 100 nM mesulergin, or with 1 nM [$^3$H]8-OH-DPAT. After rinsing 2 x for 1 minute in distilled water, the sections are dried.

Autoradiography

The slides are affixed to a tritium-sensitive film for 8 days. The film is developed for 6 minutes in D19, rinsed and fixed. The autoradiographs are quantified with a video system for image analysis (Ségu et al., 1990).

B. Results

Ircubation in the presence of 2 nM [$^3$H]5-HT (FIG. 7A) shows substantial labelling of the hippocampus and the substantia nigra. Under these conditions, all the types of 5-HT$_{1A}$ sites are labelled.

Incubation in the presence of 1 nM [$^3$H]8-OH-DPAT (FIG. 7B), which only labels the 5-HT$_{1A}$ sites, shows intense labelling of the hippocampus but not the substantia nigra.

In the case of incubation in [$^3$H]5-HT in the presence of 100 nM 8-OH-DPAT and mesulergin (FIG. 7C), only the 5-HT$_{1D}$ sites are labelled. The autoradiographs show a strong reaction with the substantia nigra.

Incubation in 0.02 nM S—CM-G[$^{125}$I ]TNH$_2$ by itself (FIG. 7D) shows virtually exclusive labelling of the substantia nigra, as in the previous case. This O-carboxymethylated derivative of serotonin binds to the 5-HT$_{1D}$ sites.

If the binding of 0.02 nM S—CM-G[$^{125}$I9 TNH$_2$ is displaced with serotonin, an IC$_{50}$ (concentration which inhibits 50% of the binding) of the order of 5 nM is obtained, therefore showing that the binding of the derivative is specific for the 5-HT$_{1D}$ sites.

Conclusion

S—CM-G[$^{125}$I]TNH$_2$ is a marker for 5-HT$_{1D}$ receptors. Any analogous molecule will therefore have this property of binding to the 5-HT$_{1D}$ sites.

5. Analysis of the S—CM-G[$^{125}$I)TNH$_2$ binding sites in man a) Postmortem human brains are stored at −20° C. 10 μm sections are prepared from blocks containing either the locus niger or the Ammon's horn. The sections are treated as indicated in 4. for the monkey brain sections.

b) After autoradiography, strong labelling is observed on the locus niger (structure corresponding to the substantia nigra in the rat) and weak labelling is observed on the Ammon's horn (equivalent in man to the hippocampus in the rat).

The locus niger contains virtually exclusively binding sites of the 5-HT$_{1D}$ type, whereas the Ammon's horn is composed predominantly of sites of the 5-HT$_{1A}$ type.

The iodinated derivative tested therefore labels the 5-HT$_{1D}$ receptors of the human brain in vitro. Thus it can be used to study receptors of this type in man and their variation in neurodegenerative diseases (Huntington's chores). The derivatives described in the present patent which have this property and which pass through the blood-brain barrier may be used for therapeutic purposes in the case of dysfunctions associated with the type of receptor in question (5-HT$_{1D}$).

III Binding of Serotonin Derivatives to Peripheral Receptors

1. Passage across the blood-brain barrier

If the molecules pass through the blood-brain barrier, they are capable of acting on the receptors of the central nervous system, an effect which has been researched in numerous cases (cf. point 4.).

In the case where receptors exist both in the peripheral nervous system and in the central nervous system, it may be desirable to have derivatives which do not pass through the blood-brain barrier. These derivatives will then have an effect on the peripheral receptors without a predominant central action.

A. Experimental Protocol 2 mice and 2 guinea-pigs are deeply anaesthetized with chloral hydrate (intraperitoneal injection of 0.12 ml of a 35% solution per 100 g of body weight). The rib cage is opened and the heart is revealed.

The mice and guinea-pigs receive intracardiac injections of 200 μl and 1.5 ml, respectively, of S—CM-G[$^{125}$I]TNH$_2$.

After 10 minutes, the animals, still under deep anaesthesia, are decapitated and the brains are frozen and stored as indicated in Example 1.

Sections are prepared and autoradiography is carried out as described in Example 1.

B. Results

An examination of sections corresponding to different regions of the brain shows no labelling, particularly in the substantia nigra, an anatomical structure which is well labelled when incubation is carried out in vitro in the same tracer.

Conclusion

The serotonin derivative tested does not cross the blood-brain barrier, making it possible to alleviate the most painful effects of migraine. No toxicity was observed at the dose injected.

2. Study of the distribution of the binding of the derivative S—CM-G[125]TNH$_2$ by visualization in vivo with a gamma camera Given that this derivative does not pass through the blood-brain barrier, as shown in 1., the distribution of the peripheral labelling was studied by visualization in vivo.

The animals (mice) are anaesthetized and injected intravenously with the derivative S—CM-G[$^{125}$I]TNH$_2$. The product is very quickly observed to diffuse into the heart, the entire vascular system and the liver. 10 minutes after the injection, the labelling decreases in the vascular system, except for the heart and the cerebral vascular system. In this latter zone, the labelling is retained for 15 to 20 minutes before slowly disappearing. The labelling of the bladder increases in the longer term, the heart remaining labelled for a fairly long time.

An experiment was performed with an iodinated derivative which exhibited the same specific binding as the above derivative but did not possess the property of binding specifically to the central 5-$HT_{1B}$ and 5-$HT_{1D}$ sites. In this case, the decline in the labelling observed with the gamma camera is identical to that observed with S—CM-G[$^{125}$I]TNH$_2$ except for the cerebral vascular system which does not exhibit any particular retention.

S—CM-GTNH$_2$ and its derivatives can therefore be used for therapeutic purposes in the alleviation of migraine attacks. Being unable to pass through the blood-brain barrier, they are not capable of causing side-effects by acting on the central serotoninergic sites in man.

EXAMPLE 3

Tablets having the following formulation were prepared:
Tryptamine 5-O-carboxymethylglycyltyrosinamide (Serotonin-CM-GTNH$_2$) . . . 0.5 mg
excipient q.s. for a finished tablet of . . . 100 mg
(details of the excipient: lactose, starch, talc, magnesium stearate)

EXAMPLE 4

Divisible tablets having the following formulation were prepared:
Tryptamine 5-O-carboxymethylglycyltyrosinamide (Serotonin-CM-GTNH$_2$) . . . 2 mg
excipient q.s. for a finished tablet of 100 mg
(details of the excipient: lactose, starch, talc, magnesium stearate)

EXAMPLE 5

An injectable preparation having the following formulation was prepared:
Tryptamine 5-O-carboxymethylglycyltyrosinamide (Serotonin-CM-GTNH$_2$) . . . 2 mg
excipient: water for injectable preparations . 2 ml

EXAMPLE 6

A nasal aerosol having the following formulation was prepared:
Tryptamine 5-O-carboxymethylglycyltyrosinamide (Serotonin-CM-GTNH$_2$) . . . 30 mg
excipient: aqueous solution: sodium chloride, trisodium citrate, citric acid distilled water . . . 15 ml

EXAMPLE 7

A buccal aerosol having the following formulation was prepared:
Tryptamine 5-O-carboxymethylglycyltyrosinamide (Serotonin-CM-GTNH$_2$) . . . 60 mg
excipient: aqueous solution: citric acid, ethyl alcohol, sweetener, flavouring, polysorbate 80, propylene glycol purified water . . . 50 ml propellant: nitrogen

EXAMPLE 8:

Kit for analyzing a 5-$HT_{1D}$ receptor

A kit was prepared for studying the presence of the 5-$HT_{1D}$ receptor and the affinity of derivatives for said receptor, and for revealing changes in the affinity and number of these receptors, said kit having the following composition:
Product of Example 2, stage B (2000 Ci/mmol), in 50 mM Tris-HCl buffer pH 7.4 . . . 15 ml
Standard: lyophilized serotonin (oxalate), 10 nmol, and buffer pH 6.2
Standard: product of Example 2, stage B, 1 nmol of serotonin per vial, and buffer pH 6.2
Inhibitor solution: 1.25 mmol of pargyline, 12.5 mmol of 8-OH-DPAT, 12.5 nmol of mesulergin per vial buffer pH 7.4
Diluent: saline buffer pH 7.4
Filters: glass fibre

BRIEF DESCRIPTION OF THE DRAWINGS

FIGURE CAPTIONS

Figure 1A:
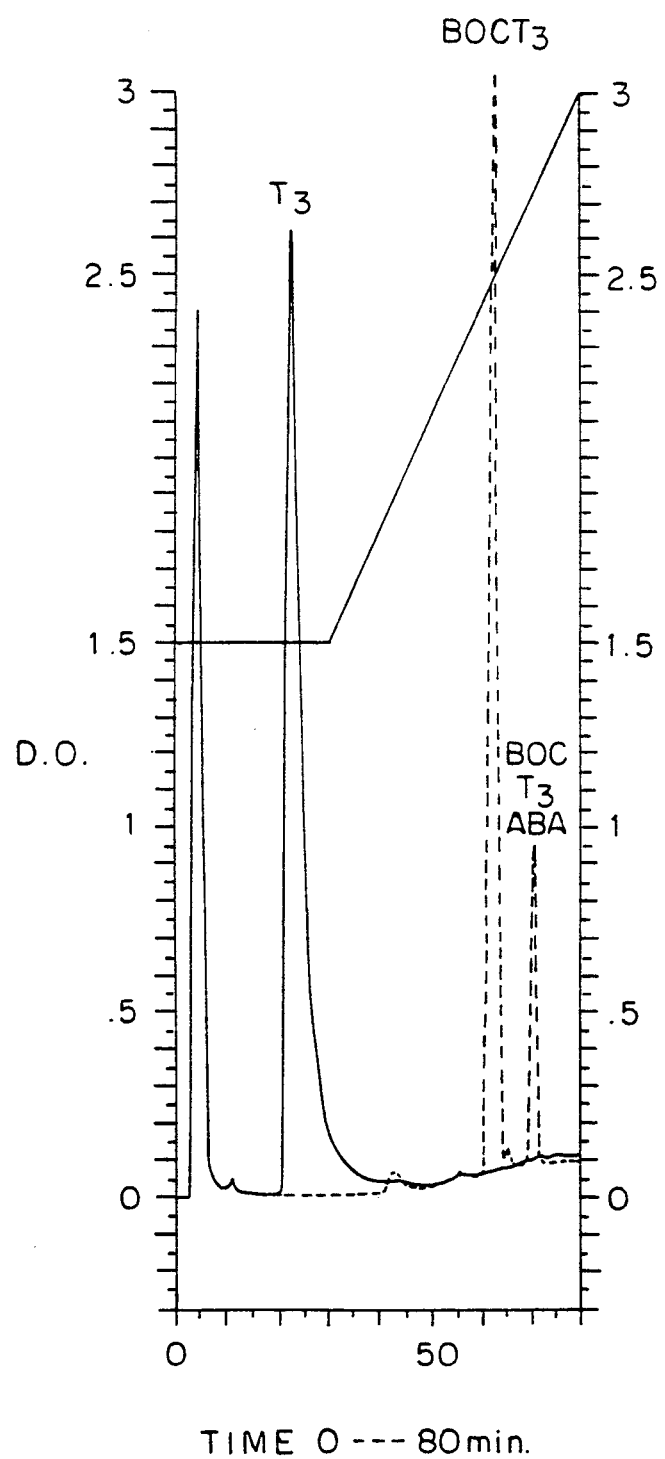
Figure 1B:
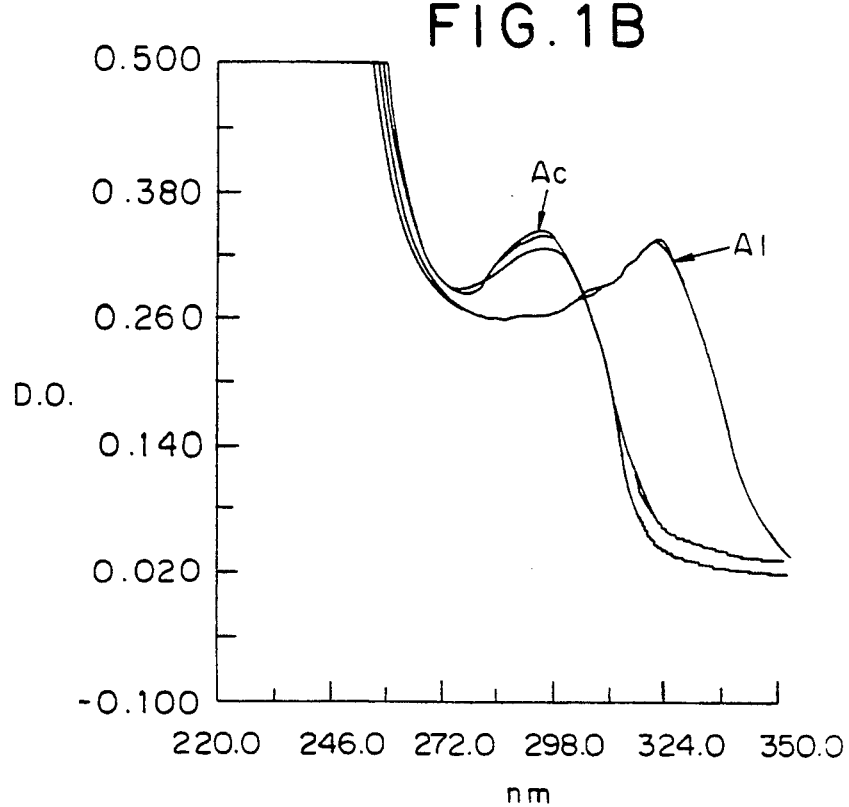

FIG. 1: Purification of the carboxymethylation products of N-BOC-T$_3$

A: chromatogram after HPLC on $\mu$ Bondapack $C_{18}$. 0–30 min: 50 vol. of 0.05% TFA, 50 vol. of methanol. 30–80 min: 100% methanol gradient.

The peak heights are not absolute because there are two different superimposed elution profiles.

B: absorption spectrum of BOC-T$_3$ in an acid medium (Ac) and an alkaline medium (Al). Ordinate: O.D. Abscissa: wavelengths from 220 to 350 nm.

The spectrum can be shifted in a basic medium, as for T$_3$.

C: absorption spectrum of BOC—T$_3$—OCH$_2$—COOH in an acid medium (Ac) and an alkaline medium (Al). Ordinate:

O.D. Abscissa: wavelengths from 220 to 350 nm.

The spectrum cannot be shifted in a basic medium.

FIG. 2: Purification of the carboxymethylation products of serotonin-N-BOC (BOC-S)

A: chromatogram after HPLC on Ultrasphere ODS $C_{18}$ with isocratic elution: 55 vol. of $H_2O$/0.05% TFA, 45 vol. of methanol. ordinate: optical density (O.D.) for various wavelengths (I)m) (indicated on the right). Abscissa : time in minutes.

B: absorption spectrum, adjusted at 280 nm, of the product emerging after 28 minutes, BOC-S (solid line), and the product emerging after 36 minutes, BOC-S-CM (dotted line). Ordinate: O.D. Abscissa: wavelengths from 200 to 350 nm.

C: absorption spectrum of BOC-S-CM in an acid medium (Ac) and an alkaline medium (Al). ordinate: O.D. Abscissa: wavelengths from 200 to 350 nm.

D: absorption spectrum of serotonin in an acid medium (Ac) and an alkaline mediu,,n (Al). ordinate: O.D. Abscissa: wavelengths from 200 to 350 nm.

E: absorption spectrum of BOC-S in an acid medium (Ac) and an alkaline medium (Al). Ordinate: O.D. Abscissa: wavelengths from 200 to 350 nm.

Note that the spectrum is shifted in a basic medium, as for serotonin (FIG. 1D). This is not the case with BOC-S-CM (FIG. 1C), which is substituted on the OH.

FIG. 3: Purification of the conjugation products of BOC-S-CM and GTNH$_2$

A: chromatogram after HPLC on Ultrasphere $C_{18}$ with isocratic elution: 60 vol. of $H_2O$ pH 6, 40 vol. of methanol. Ordinate: O.D. for various wavelengths (rim) (indicated on the right). Abscissa : time in minutes.

B: absorption spectrum, adjusted at 280 nm, of the product emerging after 18 minutes, GTNH, (solid line), the product emerging after 35 minutes, BOC-S-CM (dotted line), and the product emerging after 48 minutes, BOC-S-CM-GTNH$_2$ (dashed line). Ordinate: O.D. Abscissa: wavelengths from 200 to 350 nm.

C: absorption spectrum of BOC-S in an acid medium (Ac) and an alkaline medium (Al). Ordinate: O.D. Abscissa: wavelengths from 200 to 350 nm.

D: absorption spectrum of GTNH$_2$ in an acid medium (Ac) and an alkaline medium (Al). Ordinate: O.D. Abscissa: wavelengths from 200 to 350 nm.

E: absorption spectrum of BOC-S-CM-GTNH$_2$ in an acid medium (Ac) and an alkaline medium (Al). ordinate: O.D. Abscissa: wavelengths from 200 to 350 nm.

Figure 1C:
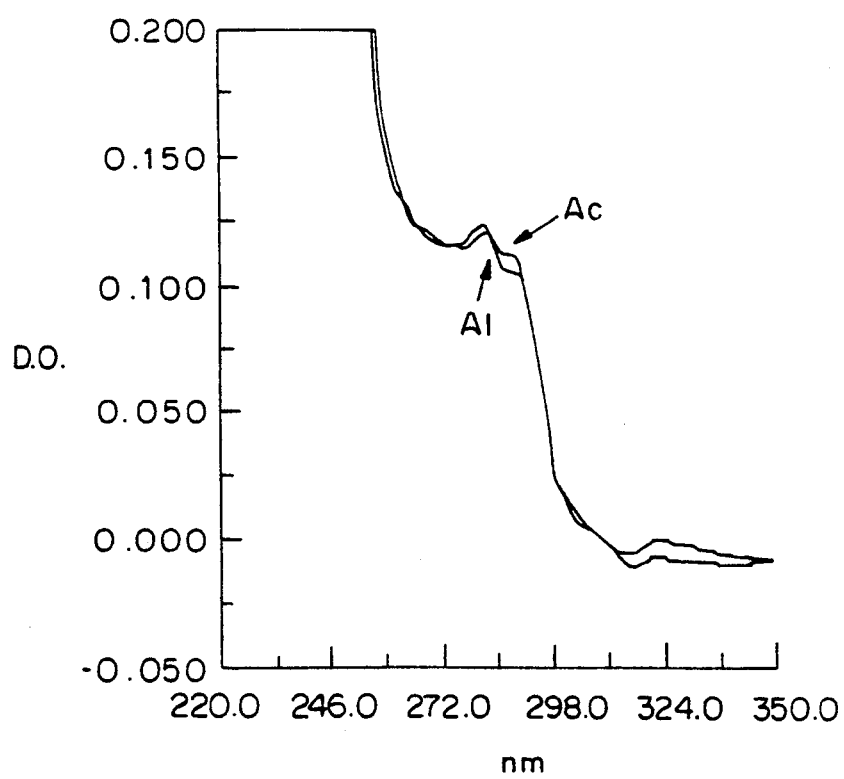

Note that the spectral shift in an alkaline medium does not correspond at all to that of a serotonin unsubstituted on the OH (FIG. 2C), whereas the spectrum ic, shifted more than that of BOC-S-CM (FIG. 1C). A shift towards the longer wavelengths is observed, as for GTNH$_2$ (FIG. 2D), but this modification is smaller in terms of O.D.

Figure 4A:
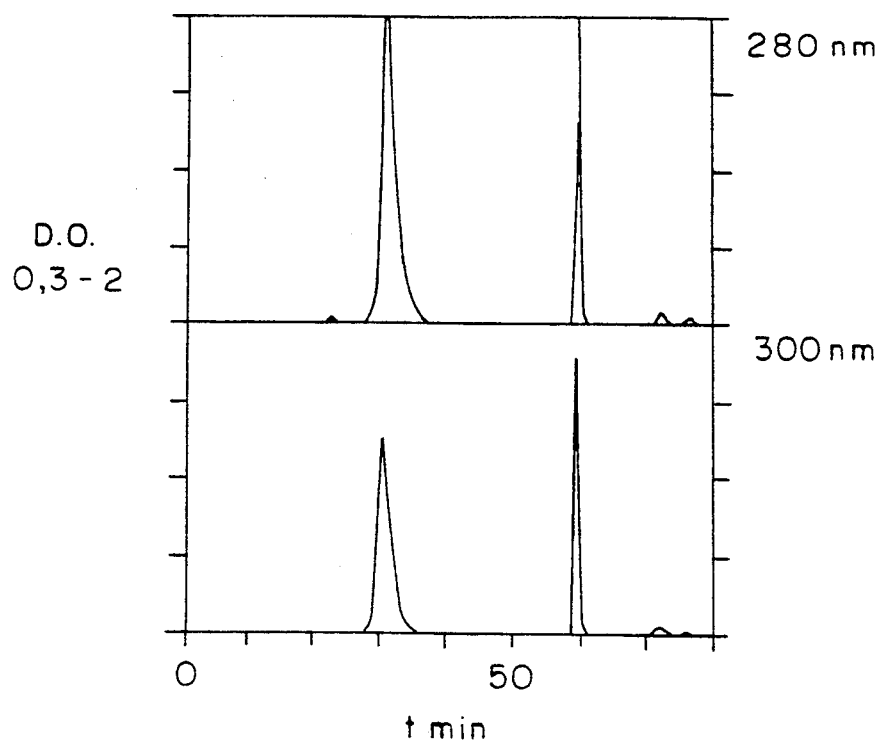
Figure 4B:
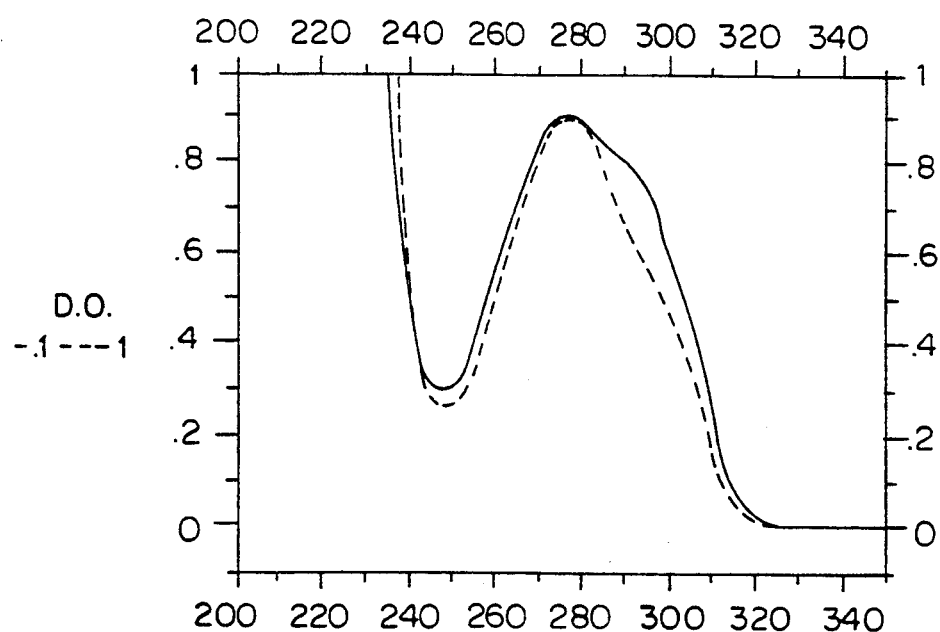
Figure 4C:
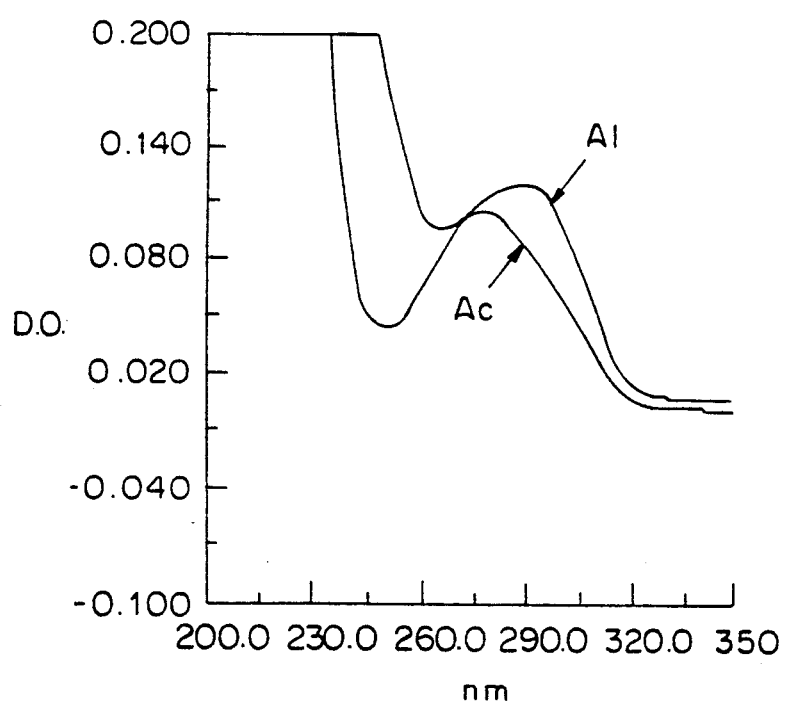

FIG. 4: Purification of the products resulting from deprotection of the amine of BOC-S-CM-GTNH$_2$ A: chromatogram after HPLC on Bondapack C.. with isocratic elution: 65 vol. of H 2O/0.05% TFA, 35 vol. of methanol. Ordinate: O.D. for 280 and 300 nm. Abscissa: time in minutes.

B: absorption spectrum, adjusted at 280 nm, of the product emerging after 24 minutes, S-CM (solid line), and the product emerging after 30 minutes, S-CM-GTNH$_2$ (dotted line).

Figure 2A:
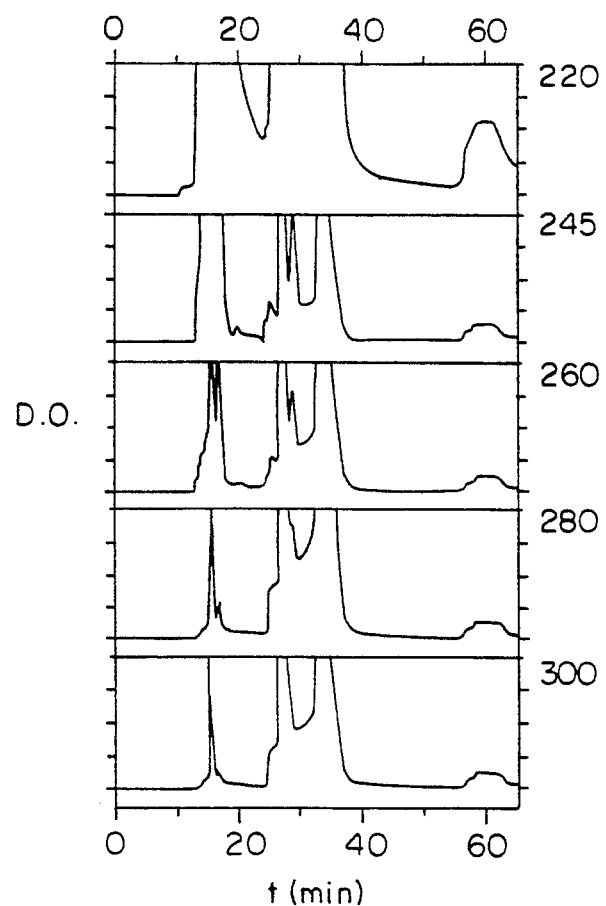
Figure 2B:
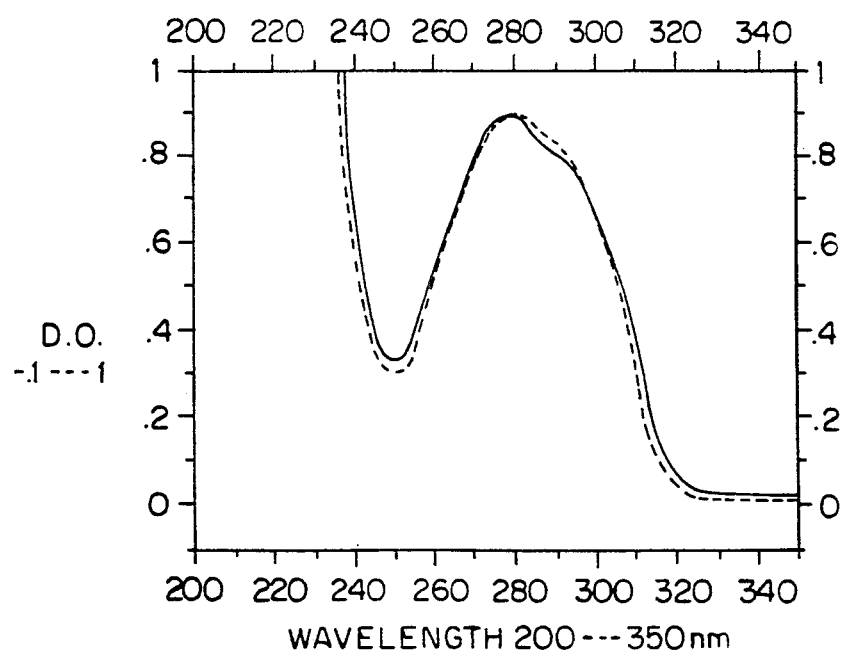
Figure 2C:
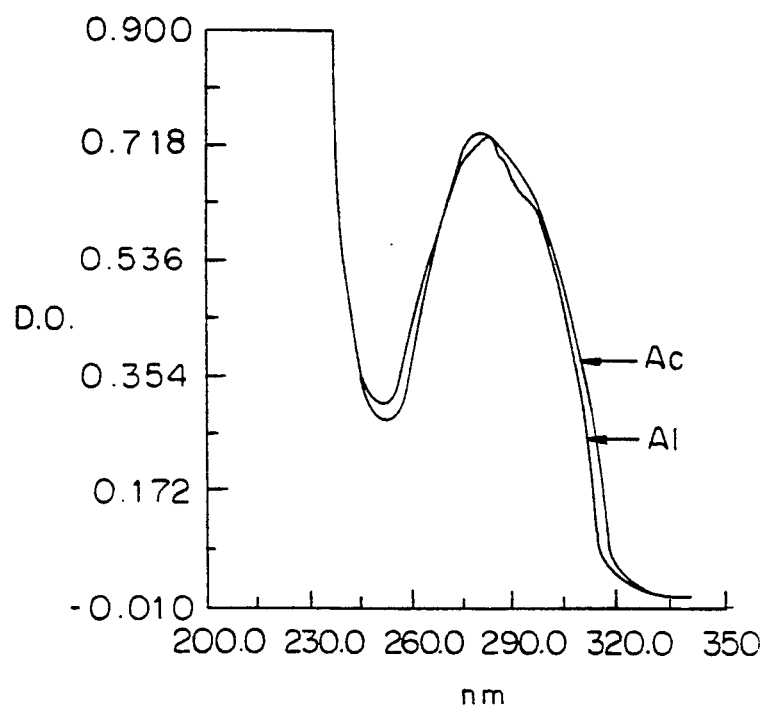
Figure 2D:
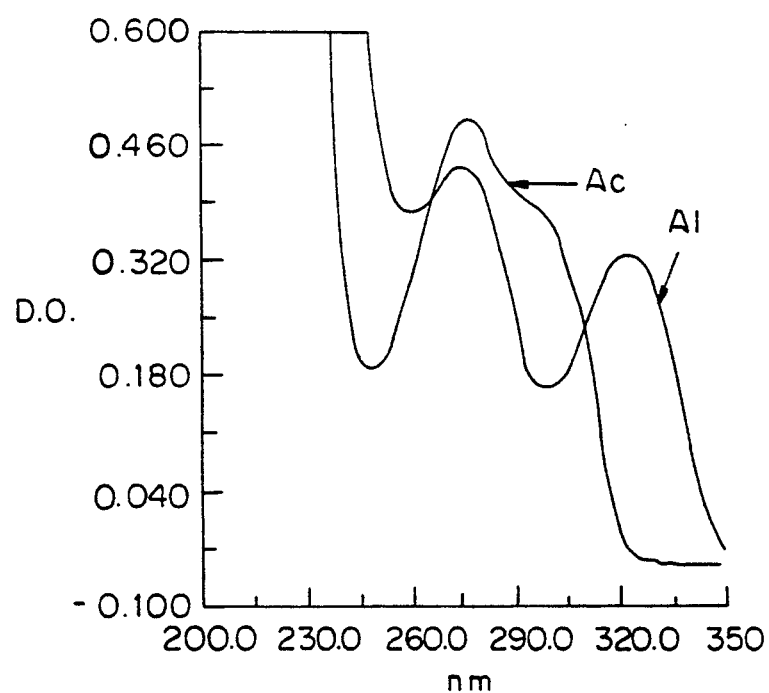

The spectrum of the product emerging after 60 minutes, BOC-S-CM-GTNH$_2$ is identical to that shown in FIG. 2B.

C: absorption spectrum of S-CM-GTNH$_2$ in an acid medium (Ac) and an alkaline medium (Al). Ordinate: O.D. Abscissa: wavelengths from 200 to 350 nm.

Figure 2E:
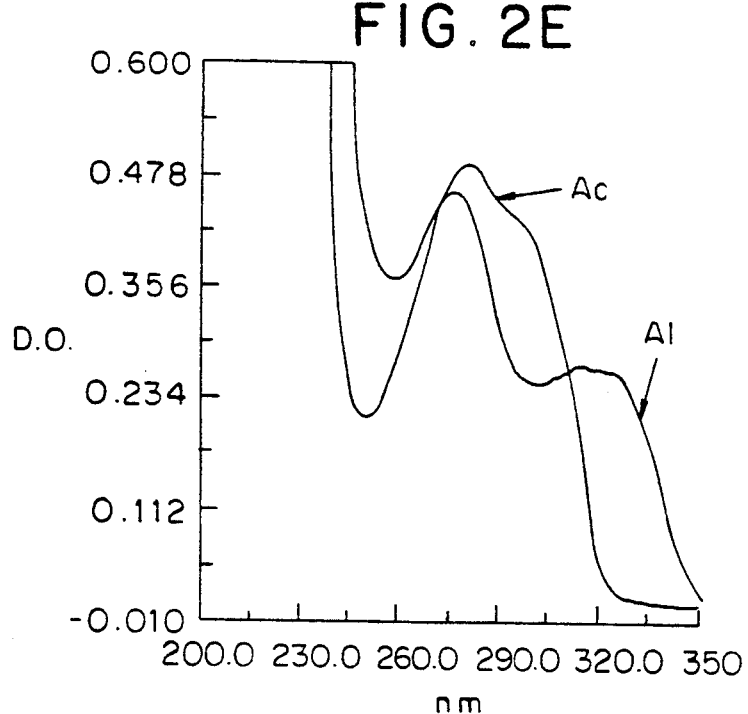
Figure 3A:
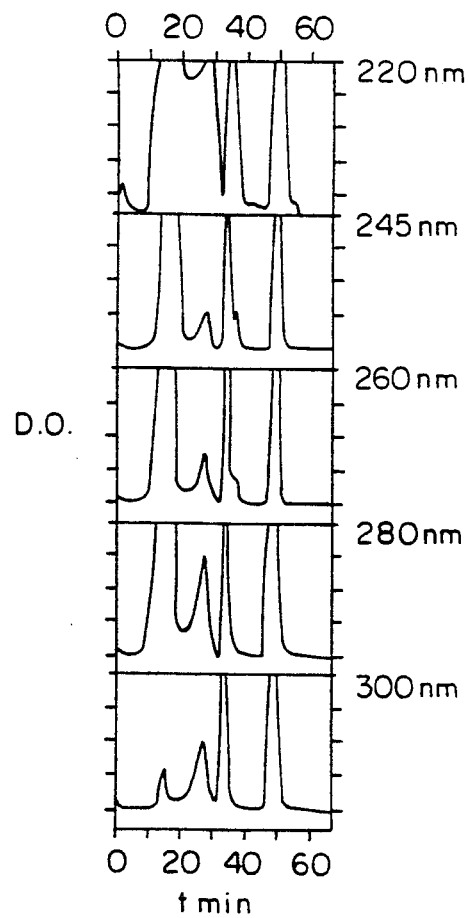
Figure 3B:
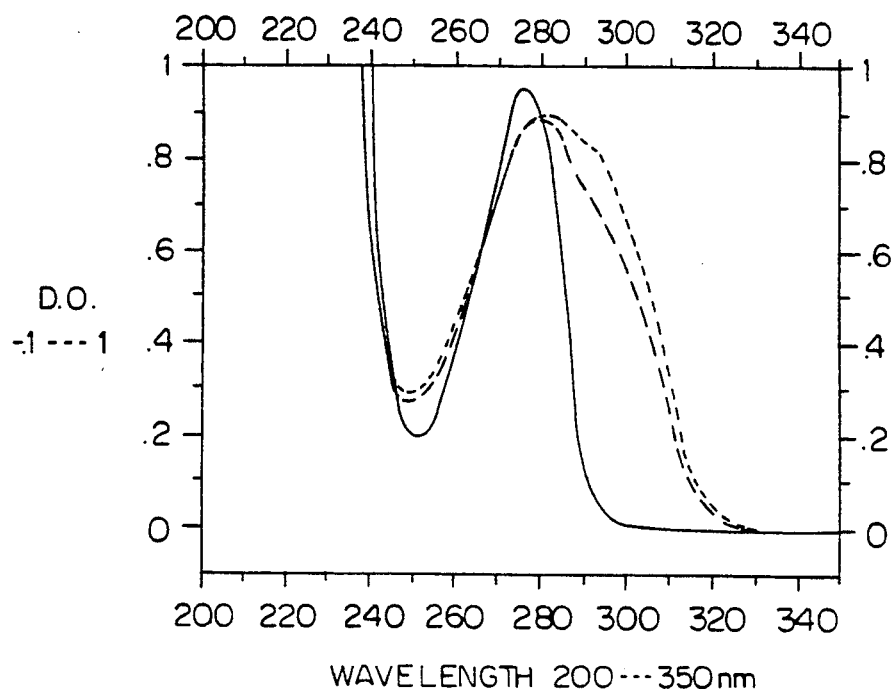
Figure 3C:
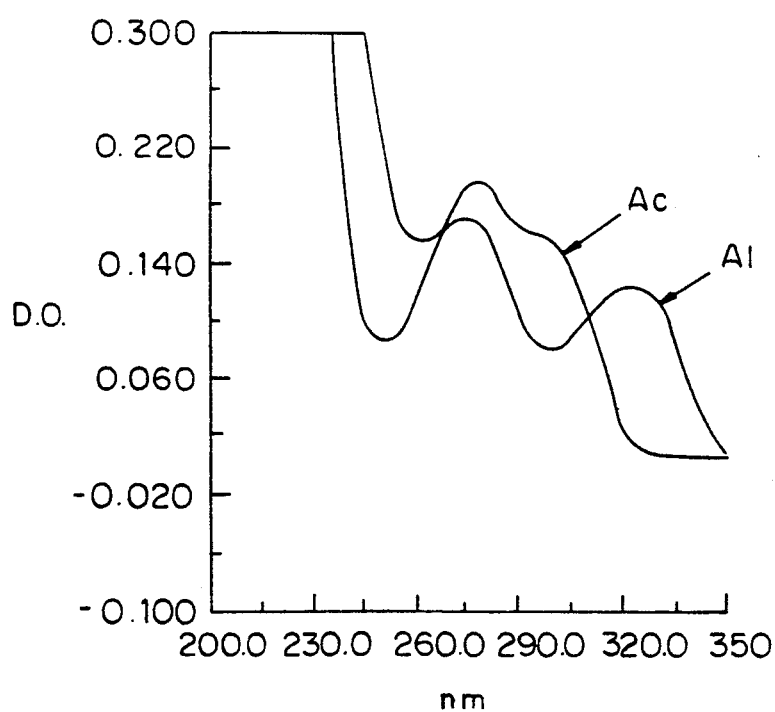
Figure 3D:
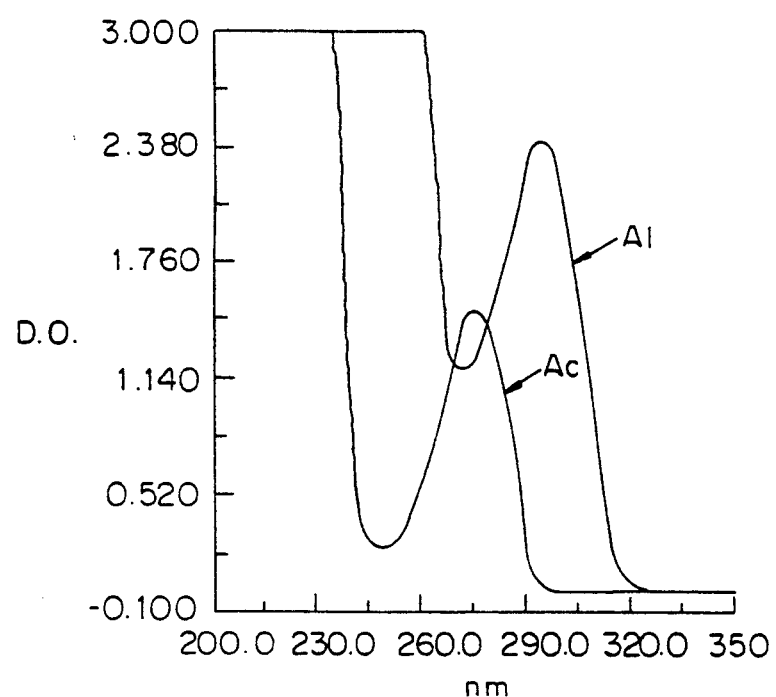
Figure 3E:
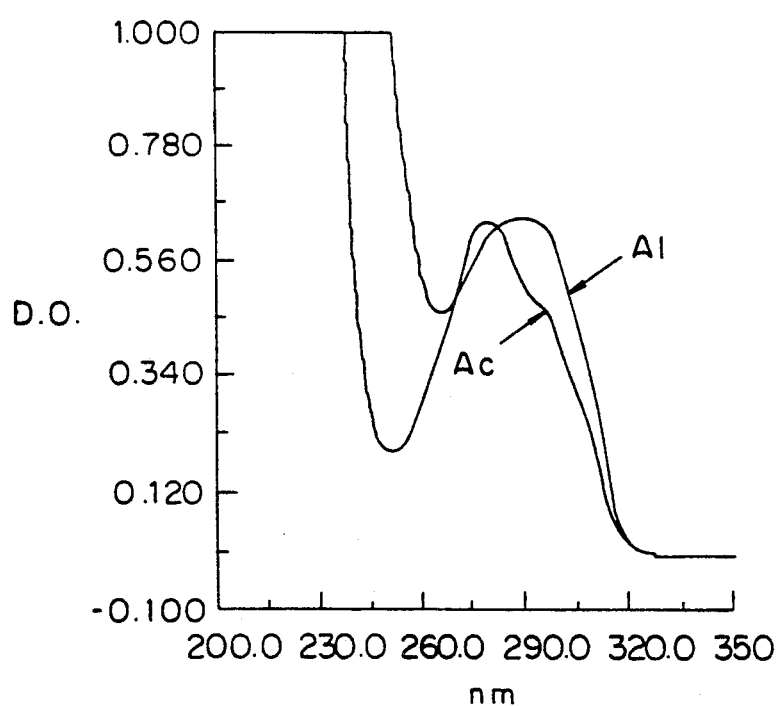

Note that the spectral shift as a function of pH is identical to that obtained for BOC-S-CM-GTNH$_2$, shown in FIG. 2E.

Figure 5C:
Figure 5B:
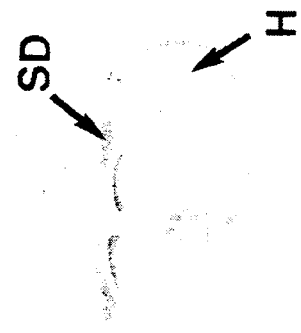
Figure 5A:
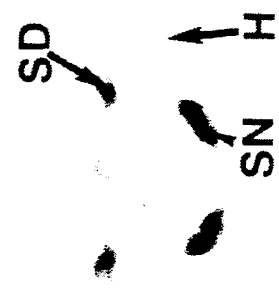

FIG. 5: Analysis of the S-CM-G[$^{125}$I]TNH$_2$ binding sites in the rat—Rat brain sections (10 μm) incubated in 0.03 nM S-CM-G[$^{125}$I]TNH$_2$ A: anterior region
Px: choroid plexus St: striatum
B: mesencephalic region
SD: dorsal subiculum; SN: substantia nigra; H: hippocampus
C: non-specific binding in the mesencephalic region, established in the presence of $10^{-5}$M 5-HT Note that Px and H are not labelled (even though they respectively contain 5-HT$_{1C}$ and 5-HT$_{1B}$ sites) and that St, SD and SN (which possess 5-HT$_{1B}$ sites) are labelled.

Figure 6C:
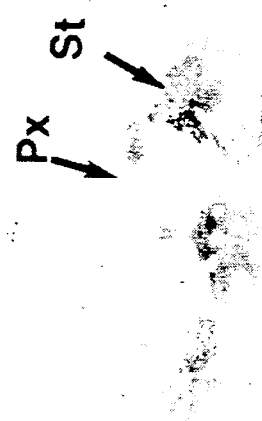
Figure 6B:
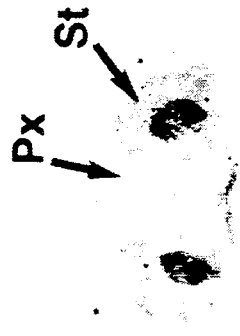
Figure 6A:
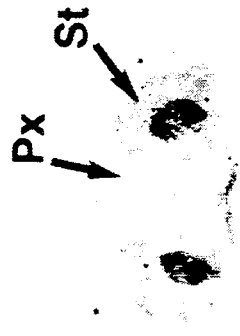

FIG. 6: Analysis of the S-CM-G[$^{125}$I]TNH$_2$ binding sites in the guinea-pig—Guinea-pig brain sections (10 μm) incubated in 0.03 nM S-CM-G[$^{125}$I TNH$_2$ A: anterior region
Px: choroid plexus St: striatum
B: region of hippocampus
SD: dorsal substantia; H: hippocampus
C: region of substantia nigra
SN: substantia nigra Note that Px and H are not labelled (even though they respectively contain 5-HT$_{1C}$ and 5-HT$_{1A}$ sites) and that St, SD and SN (which possess 5-HT$_1$D sites) are labelled.

Figure 7A:
Figure 7B:
Figure 7C:
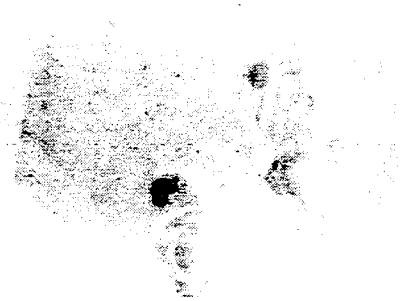

FIG. 7: Detection of the 5-HT$_1$ receptors on monkey (Macacca mulatta n.) brain sections. The frozen tissue sections (10 μm) are incubated with various probes and subjected to autoradiography.

A. Incubation in 2 nM [$^3$H]5-HT, showing the total 5-HT$_1$ sites in the hippocampus (H) and the substantia nigra (SN).

B. Incubation in 1 nM [$^3$H]8-OH-DPAT, showing the 5-HT$_{1A}$ sites exclusively located in the hippocampus.

C. Incubation in 2 nM [$^3$H]5-HT in the presence of 100 nM 8-OH-DPAT and 100 nM mesulergin, showing the 5-HT$_{1B}$ sites virtually exclusively located in "the substantia nigra.

D. Incubation in 0.02 nM [$^{125}$I]S-CM-GTNH$_2$, showing exclusive labelling of the substantia nigra, similar to that shown in C.

E. Same incubation as D, but with $10^{-5}$M 5-HT added, showing the non-specific binding (scale=1 cm).

F. Diagram of the anatomical structures, taken from section A11,5 of the atlas by Riche et al., 1968.

We claim:

1. A dimer of the formula:

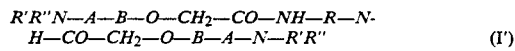

$$R'R''N—A—B—O—CH_2—CO—NH—R—N-H—CO—CH_2—O—B—A—N—R'R'' \quad (I')$$

wherein

A is a linear or branched alkylene chain of 1 to 5 carbon atoms;

B is an optionally substituted aromatic nucleus of 6 to 10 carbon atoms and optionally a heteroatom;

R is an amino acid or a polypeptide consisting of at most 5 amino acids, or an amide thereof, or an addition salt thereof with mineral or organic acid; and R' and R'' are each an alkyl radical of 1 to 5 carbon atoms or a hydrogen atoms, or an addition salt thereof with a mineral or organic acid.

2. A derivative of a biologically active molecule containing a primary amine group and a hydroxylated nucleus, or an addition salt thereof with a mineral or organic acid, of the formula I:

$$[R'R''N—A—B—O—CH_2—CO]_nR_1 \quad (I)$$

n is an integer from 1 to 10;

A is a linear or branched alkylene chain of 1 to 5 carbon atoms;

B is an optionally substituted aromatic nucleus of 6 to 10 carbon atoms and ptionally a heteroatom;

R$_1$ is an amino acid or a peptide of 2 to 10 amino acids or an amide thereof; and R' and R'' are each an alkyl radical of 1 to 5 carbon atoms or a hydrogen atom, or an addition salt thereof with a mineral or organic acid.

3. A compound according to claim 2 wherein B is indole having an halogen substituent selected from the group consisting of chlorine, bromine and iodine.

4. A derivative of formula (I) as defined in claim 2, or an addition salt thereof with a mineral or organic acid, wherein B is a phenyl or indole nucleus.

5. A derivative according to claim 2, wherein R' and R'' are alinear or branched alkyl radical containing from 1 to 5 carbon atoms and A is a radial —CH$_2$—CH$_2$—, or an addition salt thereof with a mineral or organic acid.

6. Tryptamine-5-O-carboxymethylglycyltyrosinamide or its addition salt with a mineral or organic acid.

7. A pharmaceutical composition containing, as the active principle, at least one compound as defined in claim 2.

8. A pharmaceutical composition containing, as the active principle, at least one compound as defined in claim 4.

9. A pharmaceutical composition containing, as the active principle, at least one compound as defined in claim 6.

10. An analytical kit for assaying mediators and derivatives thereof, containing at least one derivative according to claim 2.

11. A compound according to claim 4, wherein R' and R" are a linear or branched alkyl containing from 1 to 5 carbon atoms and A is —CH$_2$—CH$_2$—, or an addition salt with an acid.

12. An analytical kit for assaying mediators and derivatives thereof, containing a compund according to claim 4.

13. Tryptamine 5-O carboxymethyl tyrosylglycinamide or an addition salt thereof with a mineral or organic acid, in accordance with claim 2.

14. Tryptamine 5-O carboxymethylglycyliodotyrosinamide or an addition salt thereof with a mineral or organic acid, in accordance with claim 2.

15. Tryptamine 5-O carboxymethyl iodotyrosylglycinamide or an addition salt thereof with a mineral or organic acid, in accordance with claim s.

16. A compound according to claim 2, wherein $R_1$ is a low molecular weight group of the formula —NHR wherein R is an amino acid or a polypeptide containing 2-10 amino acids.

17. A compound selected from the group consisting of 5-O-carboxymethyltryptamine and conjugates thereof with glycyl-tyrosinamide, histamine, Tyr-Gly, Gly-Tyr, Gly-Gly, Gly-Cys, Gly-TyrNH$_2$, Tyr-GlyNH$_2$, and iodinated derivatives of said conjugates containing histamine or tyrosine; and Tryptamine-5-O-carboxymethylglycyltyrosinamide.

18. A compound according to claim 12 wherein B is bromo substituted indole.

* * * * *